United States Patent [19]
Prorok et al.

[11] Patent Number: 5,864,065
[45] Date of Patent: Jan. 26, 1999

[54] TEST APPARATUS FOR A RAILWAY WHEEL

[75] Inventors: Raymond F. Prorok, Aurora; Christopher J. Kuznieski, Posen; William J. Kucera, Elmhurst, all of Ill.

[73] Assignee: Amsted Industries Incorporated, Chicago, Ill.

[21] Appl. No.: 977,775

[22] Filed: Nov. 25, 1997

(Under 37 CFR 1.47)

[51] Int. Cl.$^6$ .......................... G01N 29/10; G01N 29/26
[52] U.S. Cl. ................................ 73/622; 73/620; 73/598; 73/637
[58] Field of Search .............................. 73/597, 598, 620, 73/621, 622, 624, 625, 627, 628, 637, 640, 641, 644

[56] References Cited

U.S. PATENT DOCUMENTS

| | | | |
|---|---|---|---|
| 3,596,503 | 8/1971 | Gay et al. | 73/625 |
| 3,812,708 | 5/1974 | Cowan et al. | 73/598 |
| 3,978,712 | 9/1976 | Cowan et al. | 73/598 |
| 4,050,292 | 9/1977 | Bloch | 73/602 |
| 5,363,702 | 11/1994 | Catot et al. | 73/598 |
| 5,574,233 | 11/1996 | Oliver et al. | 73/865.8 |

OTHER PUBLICATIONS

"USD 15" Bulletin awt 10894/06–94/5.000 GP82, to Krautkramer GmbH & Co., 1994.
"WDM Ultrasonic Thickness Measurement System for Production Monitoring and Control"–SY–001, Catalog No. WPD 5M Oct. 1988 to Krautkramer Branson, 1988.

Primary Examiner—Hezron Williams
Assistant Examiner—Rose M. Miller
Attorney, Agent, or Firm—Edward J. Brosius; F. S. Gregorczyk; Stephen J. Manich

[57] ABSTRACT

A railroad wheel test apparatus for sensing and mapping the subsurface of a railroad wheel tread face has a housing assembly with a holding device, a wheel transfer arrangement, a transducer assembly, a positioning and moving table for the transducer and a control apparatus for receiving evaluation signals from the transducer and also for communicating control signals to the positioning table and wheel transfer devices as well as a drive apparatus, where the wheel is positioned in a fluid bath and while the wheel is rotated the transducer imposes an ultrasonic signal on the tread face and receives the response signal therefrom to provide a map of the tread-face subsurface structure.

6 Claims, 7 Drawing Sheets

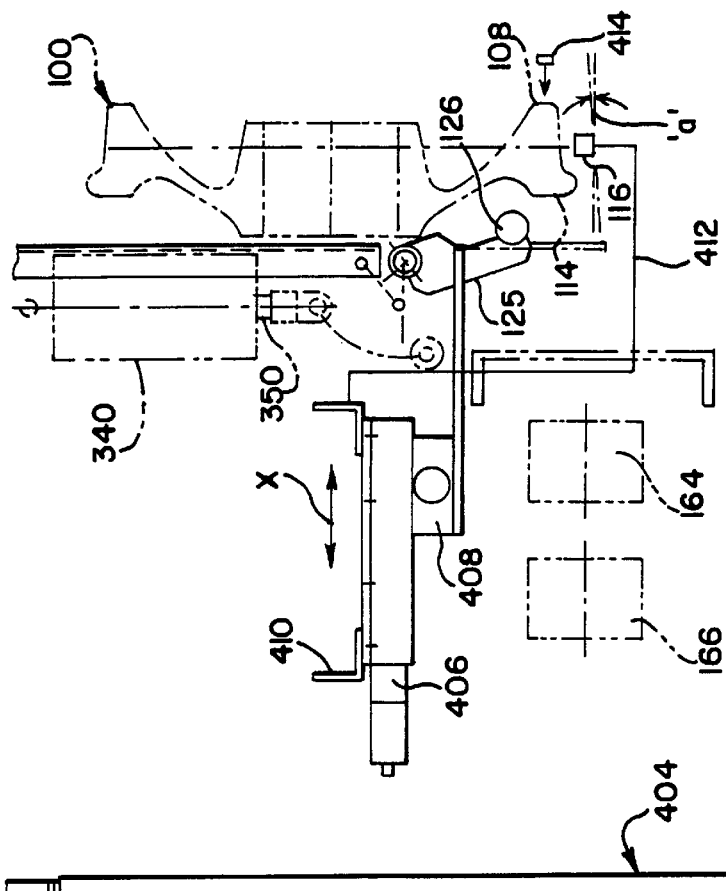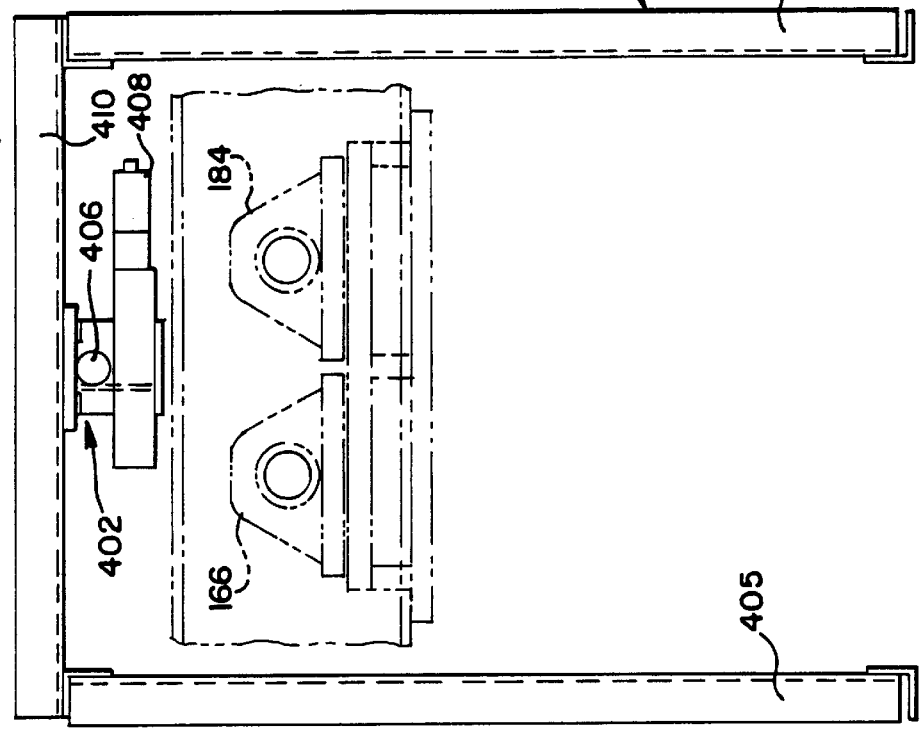

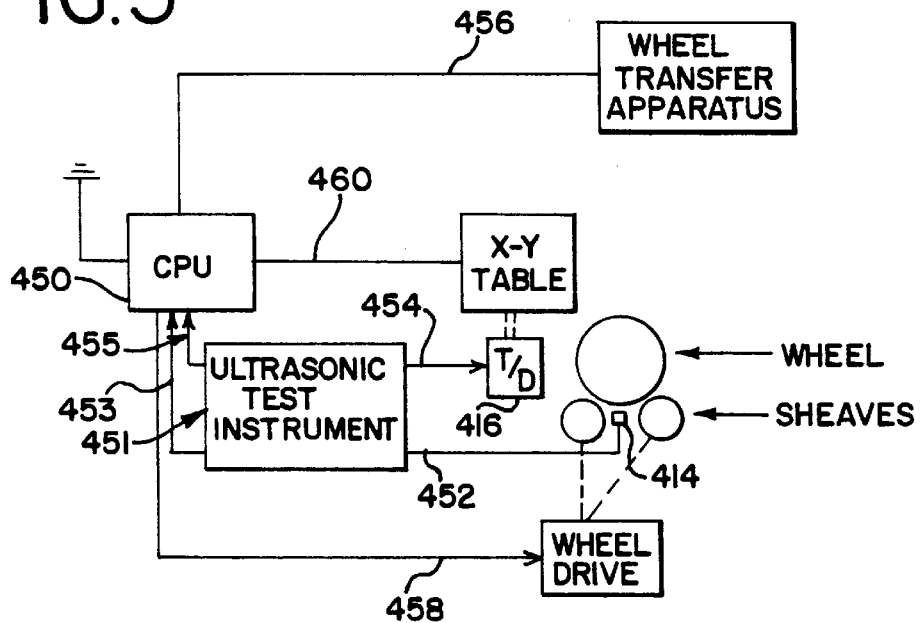
FIG.5 CONTROL OF AIR CYLINDERS
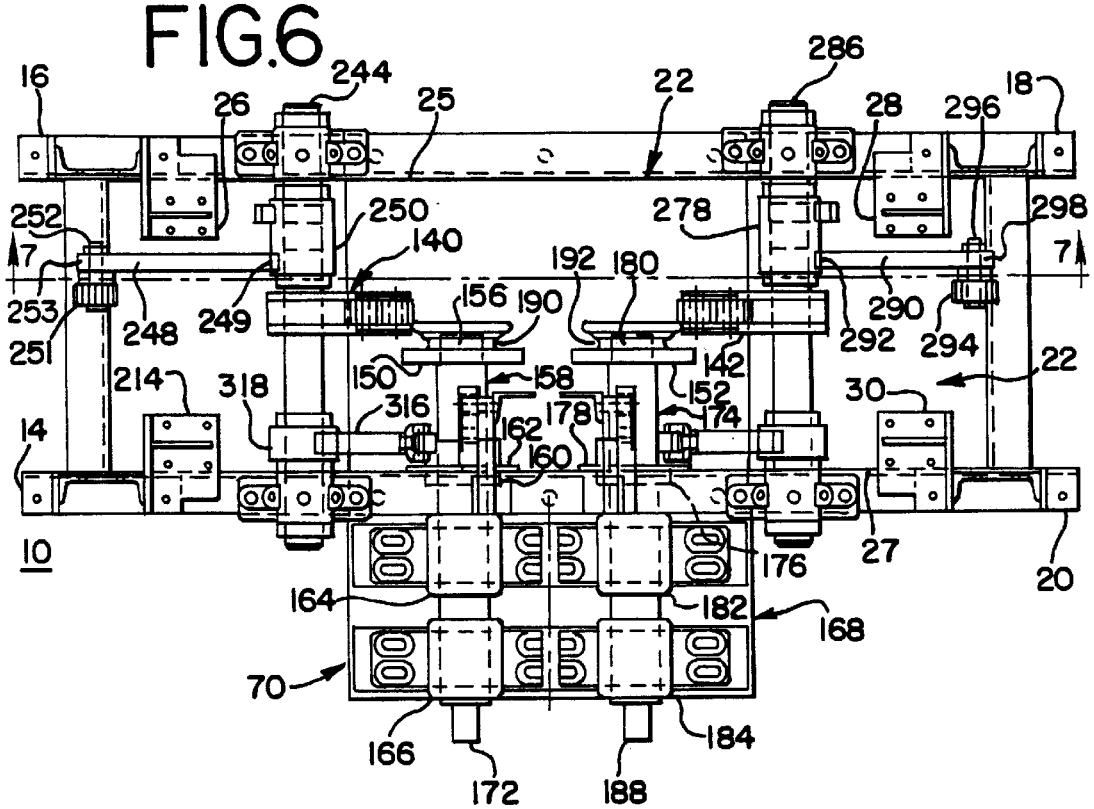
FIG.6

FIG. 10B

| | 3190 | 3191 | 3192 | 3193 | 3194 | 3195 | 3196 | 3197 | 3198 | 3199 | 3200 | 3201 | 3202 | 3203 | 3204 | 3205 | 3206 | 3207 | 3208 | 3209 | 3210 | 3211 | 3212 | 3213 | 3214 | 3215 | 3216 | 3217 | 3218 | 3219 | 3220 | 3221 | 3222 | 3223 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | | 5 | 5 | | | | | | | | | | | | | | | | | |
| | | | | | | | | | | | 5 | 6 | 6 | 7 | 9 | 9 | 10 | 9 | 9 | 9 | 8 | 8 | 7 | 6 | 5 | 5 | | | | | | | | |
| | 8 | 7 | 7 | 7 | 6 | 5 | 5 | 5 | | 5 | 5 | 5 | | | | | | | | 6 | 7 | 9 | 10 | 11 | 12 | 13 | 13 | 12 | 13 | 11 | 10 | 9 | 9 | 7 |
| | 7 | 7 | 8 | 8 | 7 | 7 | 6 | 5 | 5 | 5 | | | | | | | | | 5 | 5 | 5 | 5 | 6 | 7 | 8 | 10 | 11 | 12 | 13 | 13 | 13 | 14 | 13 | 12 | 12 | 11 |
| | 5 | 5 | 5 | 6 | 5 | 5 | 6 | 5 | | | | | | | | | | | 5 | 6 | 7 | 8 | 9 | 9 | 10 | 11 | 12 | 11 | 11 | 11 | 9 | 8 | 7 | 6 | 5 |
| | 6 | 5 | 5 | | | | | | | | | | | | | | | | | | | | | 5 | 5 | 5 | 6 | 6 | 6 | 6 | 7 | 7 | 7 | 6 | 5 | 5 |
| | | | | | | | | | | | | | | | 5 | | | | | | | | | | | | | | | | | | | |
| 31* | 24* | 25* | 21* | 24* | 29* | 28* | 22* | 19* | 19* | 15* | 19* | 19* | 18* | 19* | 13* | 22* | 22* | 29* | 27* | 31* | 33* | 36* | 39* | 41* | 41* | 37* | 36* | 40* | 38* | 37* | 34* | 33* | 30* |

5,864,065

TEST APPARATUS FOR A RAILWAY WHEEL

BACKGROUND OF THE INVENTION

The present invention relates to a test apparatus for a railway wheel. More specifically, the test apparatus provides an ultrasonic map of the subsurface structure of the wheel for both a quality control analysis of such structure and as a historical record of the structure for post-service analysis.

Railway wheels are generally either wrought or cast steel, although cast iron wheels were utilized during the nineteenth century. Railway wheels, as test pieces, may be broadly described as large, heavy, awkward and cumbersome elements, which may weigh between 700 and 1000 pounds, for example. Analysis and inspection techniques for these wheels generally may be considered to have historically evolved from the following methods: (1) visual inspection; (2) physical testing, including microstructure analysis by destructive testing on a random sampling basis; (3) magnetic particle testing for surface flaws such as "heat checks"; and, (4) ultrasonic testing for microstructure analysis. This historical listing is not exhaustive of all test methods, but it illustrates the progression of the analytical and testing procedures utilized in the analysis of railway wheels.

The initial introduction of an ultrasonic analysis technique for the railway wheel tread face utilized two transducers in various fixed locations in a test stand, which transducers were provided around the tread circumference. A refinement to this initial test apparatus utilized four, and then eight transducers in a similar configuration to provide a more complete analysis of the wheel perimeter. However, this assemblage again utilized discrete locations around the wheel perimeter. Each of these methods utilized only two rim face transducers, and the remaining two, four or eight transducers in the array are arranged to sense a specific wheel component, characteristic or parameter.

As noted above, analytic test techniques are available to describe the microstructure of a wheel. However, the most generally utilized analytic method involves a sample-destructive technique. The ultrasonic technique provides discrete location analysis of subsurface anomalies, but current apparatus cannot consistently reproduce the test on the same wheel, as there is no repetitive specific locating point or reference position. Thus, repeatability of the test and the test results has been a continuing question. As noted above, it is desirable to test a railway wheel for internal soundness or wheel integrity; to establish a wheel history of each wheel; to provide a more sophisticated analytical tool for evaluating a wheel for potential rejection or discard; and, to provide these evaluations through a nondestructive method or test.

SUMMARY OF THE INVENTION

The present invention provides an apparatus to capture a railway wheel and to maintain it in a plane during the test sequence. A transducer or sensor is secured to an x-y table coupled to and driven by a microstepper motor for laterally traversing the tread surface of a wheel as it is rotated, which traces an invisible, spiral track on the tread surface. That is, as the wheel is rotated in a plane about its axle-bore axis, the transducer signal is imposed on the tread face surface from the wheel-flange face to the wheel outer face. The transducer signal is preferably imposed at a ninety degree angle or normal to the tread face. The imposed ultrasonic signal penetrates the tread surface and provides a reflected signal, which is indicative of interdendritic shrinkage or potential voids, and discontinuities within the structure. Further, the x-y table allows the operator to find or relocate at a later date, such as after a period of service, a physical position of the wheel, and consequently the wheel structure at such later time, as well as to accommodate variations in the test equipment or the railway wheels.

BRIEF DESCRIPTION OF THE DRAWINGS

In the Figures of the Drawing, like reference numerals identify like components, and in the drawing:

FIG. 3 is a front elevational assembly view, as shown in FIG. 1, of the xy frame and sensor placement apparatus;

FIG. 4 is a side elevational view of the xy frame and sensor placement apparatus of FIG. 3;

FIG. 5 is a schematic illustration of the control circuit for the present invention;

FIG. 6 is a plan view of the apparatus of FIG. 1;

DETAILED DESCRIPTION OF THE PREFERRED EMBODIMENT

Figure 1:
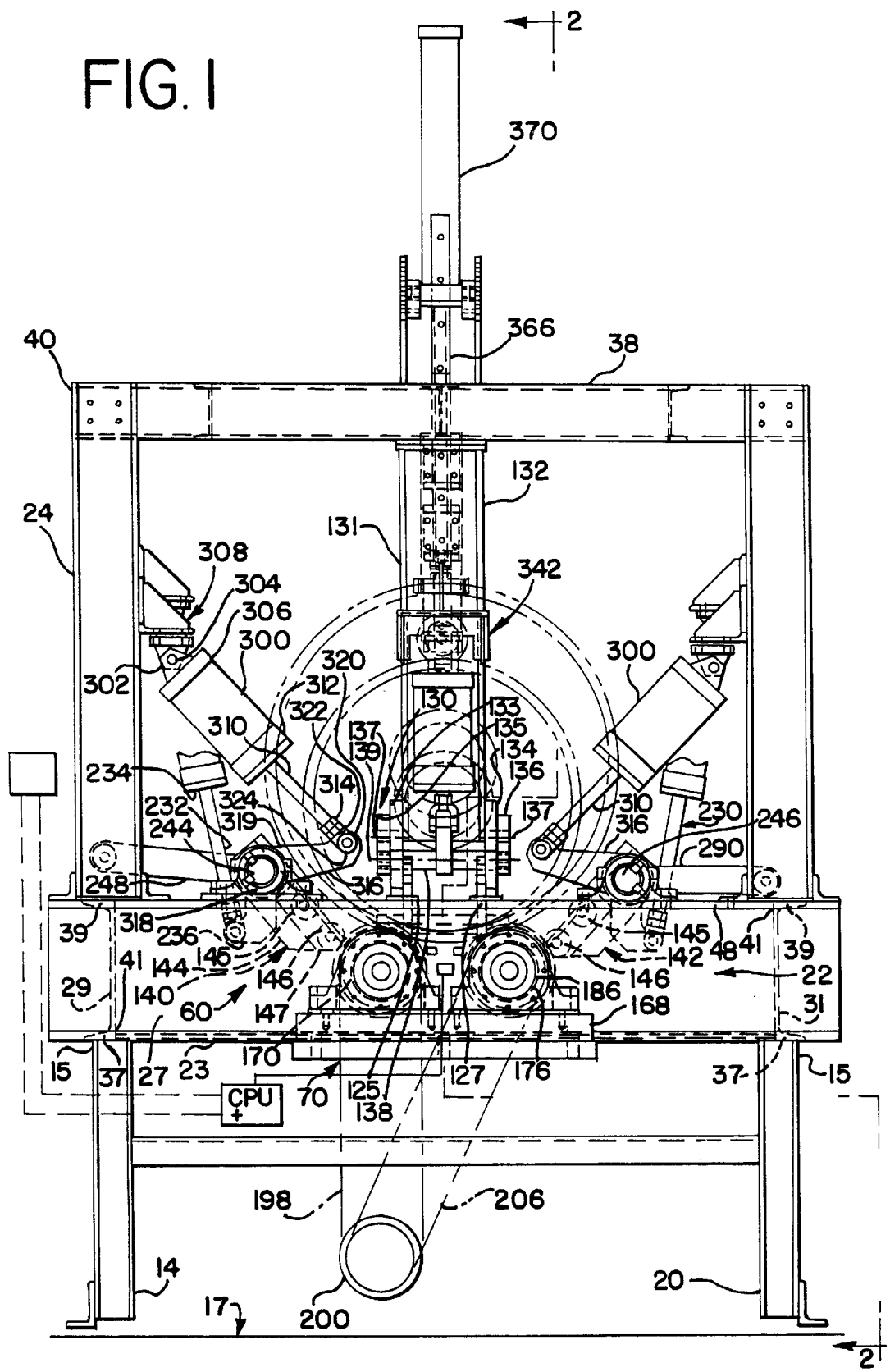
FIG. 1 is a front elevational view of the assembly with partial sectional views of the components.
Figure 9:
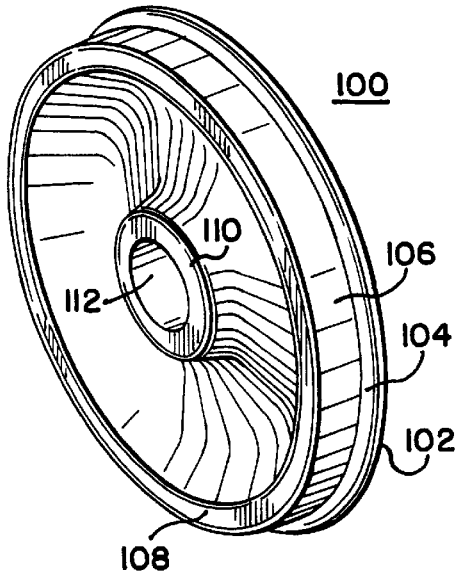
FIG. 9 is an oblique view of an exemplary railway wheel.

FIG. 1 illustrates railroad wheel sensing apparatus 10 for nondestructive evaluation and subsurface mapping of the structure of railway wheels 100, as exemplified by FIG. 9. In FIGS. 1 and 6, sensing apparatus 10 has frame assembly 12 with upright legs 14, 16, 18 and 20 anchored to floor 17, and having coupling fluid holding tank 22 mounted on legs 14 to 20 at upper leg ends 15. Tank 22, which is shown for example with a rectangular shape in FIGS. 1, 2, 6 and 7, has lower wall 23, front sidewall 25, rear sidewall 27, first endwall 29 and second endwall 31 with upper wall edge 33 and volume 35. Each sidewall 25,27 and endwall 29,31 has a lower flange 37 and an upper flange 39. At corners 41, apparatus 10 has upright arms 24, 26, 28 and 30 extending vertically upward from tank 22 and flanges 39, which arms 24, 26, 28 and 30 are connected by horizontal cross braces 32, 34, 36 and 38 at their sequential upper ends 40 of frame 12.

Apparatus 10 includes wheel handling and transfer device 60, wheel holding device 70, wheel rotating means 80 and sensing assembly 90. Each of holding device 70, rotating means 80 and assembly 90 are mounted on, or operable with, frame assembly 12 and tank 22. In a known method of wheel transfer, a rail track with guide rails (not shown) allows railway wheel 100 to roll on its tread 106 in a generally upright manner into the central portion of frame assembly 12 above tank 22 and among arms 24,26,28 and 30. Railway wheels 100 are illustrated in FIG. 9, and also in dashed outline in two different sizes in FIG. 1 to note the general position within apparatus 10.

Wheel 100 in FIG. 9 has flange 102 with flange face 104, tread 106, front face 108 and hub 110 with axle bore 112. Thus, wheel 100 can roll on tread 106 into the central portion of frame 12 to contact handling and transfer device 60.

Figure 7:
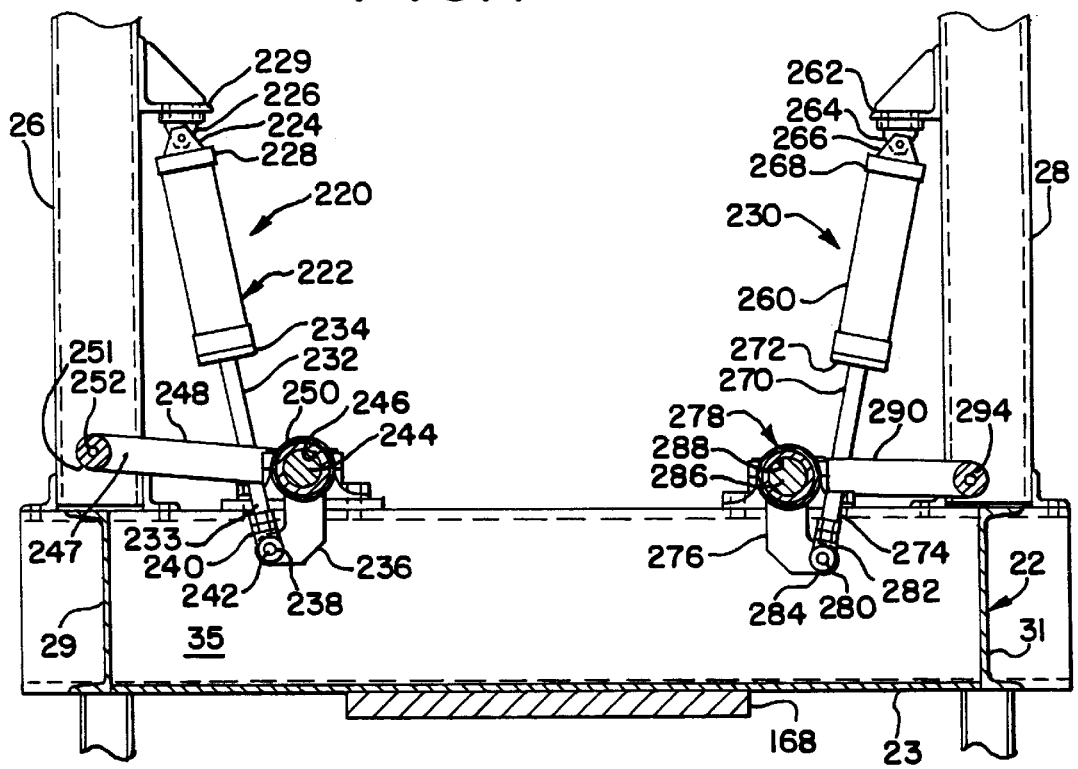
FIG. 7 is an elevational view taken along the line 7—7 in FIG. 6.
Figure 8:
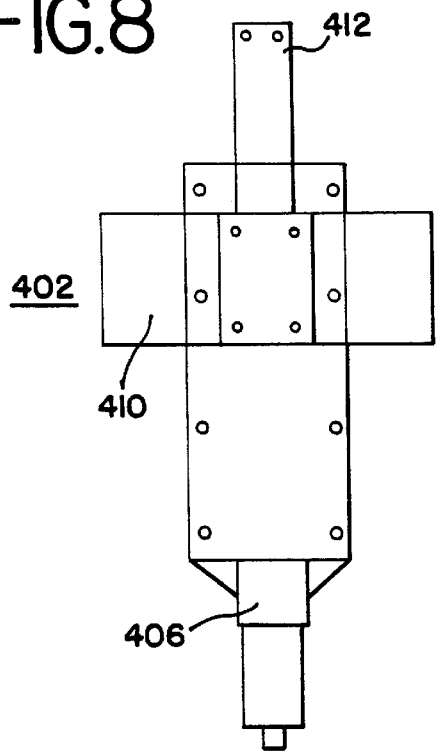
FIG. 8 is a plan view of the xy table and positioning apparatus for the sensors.

In FIGS. 1, 2, 6 and 7, handling and transfer device 60 is positioned in frame 12, and includes bridge support assembly 130, first wheel-runway assembly 140, second wheel-runway assembly 142, first roller assembly 220 and second roller assembly 230. In FIGS. 1, 6 and 7, wheel 100 enters frame assembly 12 from left to right as noted by the arrows labelled 'wheel travel', however, this travel direction and component arrangement is merely exemplary and not a limitation. Wheel 100 moves on the above-noted rail and guides (not shown) to a generally central position in frame 12 to contact handling and transfer device 60, which wheel 100 is positioned on holding device 70.

Figure 2:
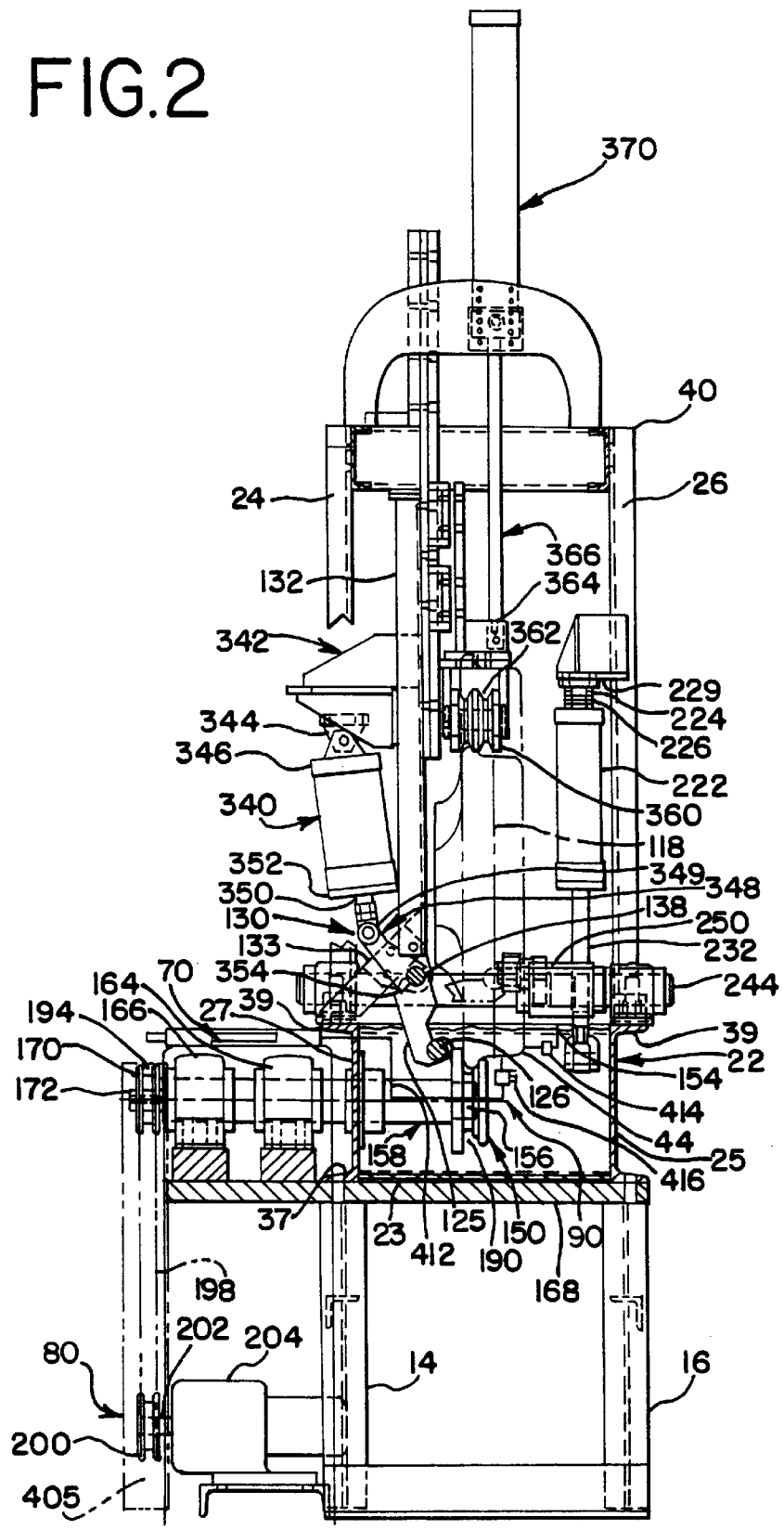
FIG. 2 is a side elevational view taken along the lines 2—2 in FIG. 1.

Holding device 70 includes first sheave or roller 150 and second sheave or roller 152 (cf., FIGS. 2 and 6) positioned below fluid surface 154 in tank 22 with coupling fluid therein. First roller 150 is mounted on first end 156 of first shaft 158 extending through first aperture 160 and seal 162 in rear sidewall 27 of tank 22. Shaft 158 outside of tank 22 extends through first pillow block and bearing 164 and second pillow block and bearing 166 mounted on bearing plate 168. Plate 168 is secured to frame assembly 12, and as shown in FIG. 2, has first sprocket 170 mounted on second end 172 of first shaft 158. Second shaft 174 in FIG. 6 is generally parallel to first shaft 158 and, extends through second aperture 176 and second bearing seal 178 in tank sidewall 27 with second roller 152 mounted on second-shaft, first-end 180 in tank 22. Second shaft 174 also extends through third pillow block and bearing 182 and fourth pillow block and bearing 184 mounted on bearing plate 168 with second sprocket 186 (cf., FIG. 1) mounted on second-shaft second-end 188.

Each of first roller 150 and second roller 152 has an arcuate indentation 190, 192, respectively, on each roller circumference, which indentations 190, 192 receive wheel flange 102 during a test of a wheel 100. Drive chain 198 extends between first sprocket 170 and third sprocket 200 coupled to drive-motor shaft 202 extending from drive motor 204. Similarly second drive chain 206 extends between drive motor 204 with third sprocket 200 and second sprocket 186, although it is recognized that a second drive motor with a separate sprocket (not shown) may be utilized for independent coupling to second sprocket 186. Alternatively, second sprocket 186 and second shaft 174 may act as an idler roller with no direct coupling to a drive motor. Each of these latter structures are noted as available alternatives. Further, drive could be provided by alternative apparatus, such as belts and sheaves.

In FIGS. 6 and 7, first roller assembly 220 has first air or pneumatic cylinder 222, pivotally coupled to upright arm 26 with clevis 224 and pin 226 at upper cylinder end 228 and first eye bracket 229. Reciprocable rod 232 is extendible from cylinder 222 at cylinder lower end 234. Bushing 250 at bore 246 has pivot arm 236, which is coupled to distal end 233 of rod 232 by second female clevis 240 and second pin 242. This coupling allows pivotal rotation of pivot arm 236 on first pivot shaft 244 by rod 232, which shaft 244 extends through second bore 246. Kicker arm 248 is coupled to bushing 250 at first kicker-arm end 249 with roller 251 secured on pin 252 at second kicker-arm end 253. Reciprocation of rod 232 induces rotation of bushing 250 and kicker arm 248 to position roller 251 in proximity to wheel 100.

Second roller assembly 230, which is juxtaposed to first roller assembly 220, is mounted in frame 12 generally between upright arms 28 and 30. Assembly 230 has air cylinder 260 pivotally coupled to second eye bracket 262 on upright arm 28 with second clevis 264 and pin 266 at second-cylinder upper end 268. Reciprocable rod 270 is extendible from second cylinder 260 at cylinder lower end 272. Distal end 274 of rod 270 is coupled to pivot arm 276 with second bushing 278 and bore 288 with female clevis 282 and pin 284 to allow pivotal rotation of pivot arm 276 on second pivot shaft 286. Second shaft 286 extends through bore 288 of bushing 278. Stopper arm 290 has its first end 292 coupled to bushing 278, and stopper arm second end 298 is secured on roller 294 with pin 296. Reciprocation of rod 270 rotates bushing 278 and stopper arm 290 to position roller 294 in proximity to wheel 100.

In FIG. 1, wheel runway assemblies 140 and 142 are similar in structure, but they are juxtaposed on either side of the wheel-test position, therefore, only assembly 140 will be described but the description will also be generally applicable to assembly 142. Air cylinder 300 of assembly 140 is pivotally coupled to upright arm 24 with clevis 302 and pin 304 at upper cylinder end 306 and third eye bracket 308. Reciprocable rod 310 with distal end 314 is extendible from lower end 312 of cylinder 300 and is coupled to pivot arm 316 at pivot arm end 322 by bushing 320 and pin 324. Pivot arm 316 at its second end 319 is secured to bushing 318 on first pivot shaft 244 at its second end. First wheel-runway assembly 140 in FIG. 1 has arm 144 with first roller 145 and second roller 146 at its distal end 147. Runway assembly arm 144 is also secured to first pivot shaft 244 and is rotatable by movement of pivot arm 316 to align rollers 145, 146 with the track (not shown) to receive wheel 100. Similarly, second runway assembly 142 has a second set of rollers 145 and 146 for receipt and transfer of wheel 100 either into or out of test stand 10. As noted above, assembly 142 is juxtaposed to assembly 140 and the direction of rotation of the reciprocating shafts and pivoting of the several components are mirror images of the direction of movement of the components of assembly 140.

Bridge support assembly 130 in FIGS. 1 and 2 has first upright support 131 and second upright support 132 downwardly extending from horizontal brace 38. Upwardly extending angle brackets 133 and 134 are mounted on rear sidewall 27, which brackets 133, 134 are connected to upright supports 131, 132, respectively. Anchoring braces 135 and 136 are positioned on the outer surfaces of brackets 133 and 134, respectively, with securing bolts 137 extending through braces, brackets and supports 131 to 136. Cross pin 138 extends through braces 135, 136 and angle brackets 133, 134 with first and second downwardly extending arms 125 and 127, respectively, having second pin 126 extending therebetween.

In practice, wheel 100 travels on a track contacting tread 106 and enters frame assembly 12 in an upright manner from the left in FIG. 1. Wheel 100 initially moves onto bridge assembly 130, and more specifically arms 125, 127 and second pin 126, which bridge assembly 130 is subsequently lowered to set wheel 100 onto first and second rollers 145, 146 of each of first and second wheel runway assemblies 140, 142. Wheel 100 is inhibited from further movement by stopper arm 290, which is moved into a stop position by extending rod 270 from cylinder 260 and rotating bushing 278 on second shaft 286. Thereafter, first and second rollers 145, 146 of wheel runway assemblies 140 and 142 lower wheel 100 onto rollers 150, 152 and are moved away from contact with wheel tread 106 and flange 102. Wheel runway assemblies 140 and 142 are rotated from retention of wheel 100 by extending rods 310 from air cylinders 300, which moves pivot arms 316 on first pivot shaft 244 or second pivot shaft 286.

Bridge assembly 130 in FIGS. 1 and 2 has air cylinder 340 secured at its upper end 346 by eye bracket 342 of clevis assembly 344, which assembly 342 is mounted on first and second upright arms 131 and 132. Connecting arm 348 is pivotally connected at its first end 349 to drive rod 350 at lower end 352 of cylinder 340 and is drivingly coupled to cross pin 138 at connecting-arm lower end 354. Extension of drive rod 350 by air cylinder 340 rotates connecting arm 348 and pin 138, which consequently rotates downwardly extending arms 125 and 127 about pin axis 139, and thereby deposits wheel 100 on or captures wheel 100 from first and second rollers 145 and 146 for transfer to and from first and second wheel runway assemblies 140, 142. Sheave 360 with indentation 362 is mounted on distal end 364 of rod 366 and is moved into position at the upper end of wheel 100 in assembly 12 by extending rod 366 from air cylinder 370. This air cylinder 370 is mounted generally between crossbraces 32 to 38 at upper end 40 of assembly 12. Wheel 100 is thus provided in an upright position within test stand or frame assembly 12. Thereafter, wheel 100 may be rotated by driving rotation of any of third sheave 170 or fourth sheave 186 from drive motor 204 and drive-belts 198, 206.

Wheels 100 are presently analyzed by fixed position sensors, which monitor the wheel and its underlying as-cast structure for voids, inclusions and discontinuities, but only at discrete, single track or single circumferential locations at the perimeter of wheel tread 106 or flange 102. However, assembly 12 has motor control tables and encoder assembly 402 in FIGS. 2, 3, 4 and 8, which includes mounting stand 404 with legs 405 and top of mounting stand top 410. Mounting stand 404 is anchored to floor 17 as noted in FIGS. 2 and 3. In the figures, apparatus 402 is positioned atop mounting stand 404 and above pillow blocks and bearings 164, 166, 182 and 184 with first or x-direction transducer-drive motor 406 and second or y-direction transducer-drive motor 408 secured to top of mounting stand 410. In this configuration, motor control tables and encoder assembly 402 are movable in the x direction by first drive motor 406, which x-direction is into the plane of the paper in FIG. 3 or horizontally along the plane as noted in FIG. 4. Similarly, second motor 408 is operable to move motor control tables and encoder assembly 402 in the y-direction as noted in FIG. 3. Drive motors 406 and 408 may be microstepper motors, such as Parker-Hannafin microstepper motors for example.

Transducer arm 412 extends from motor control table and encoder assembly 402, which is shown in a generally L-shaped form. In assembly 12, arm 412 extends downwardly into the coupling fluid of tank 22 with second transducer 416 at the end of arm 412 and in proximity to tread face 106. First transducer 414 is provided in a fixed or reference location in proximity to wheel rim face 108 as noted in FIG. 4. In this location, transducer 414 communicates a signal to ultrasonic test instrument 451 through line 452, which signal is communicated to and stored in CPU 450 by line 453. This signal provides a location for noting the relative location of the remaining components and surfaces of wheel 100. Initial set-up of CPU 450, ultrasonic test instrument 451 and apparatus 12 are accommodated by utilization of a standardized or reference railroad wheel of the same size as the wheels to be tested, which set-up provides the empirical reference parameters for the comparison of evaluation signals from transducers 414 and 416.

In the schematic illustration of FIG. 5, CPU 450 is coupled to ultrasonic test instrument 451 by lines 455 and 453, which are also coupled to transducer 414 by line 452 and to transducer 416 by line 454. Ultrasonic test instrument 451 is used to send and receive signals from transducers 414 and 416. Instrument 451 communicates signal data to CPU 450 for storage and evaluation of such data. CPU 450 is also operable as a controller to provide control signals through lines 456 to the air cylinders of assembly 12 for delivery and transfer of wheels 100 to and from unit 12; to communicate control signals through line 458 to drive motor 204 for timed rotation of wheel 100 in assembly 12; and, to provide communication to drive motors 406 and 408 through line 460. The communication between the several apparatus are schematically depicted in FIG. 5.

In the operation of the apparatus and during the analytic test, wheel 100 is introduced into apparatus 12 by rolling tread 106 of wheel 100 on a track (not shown) into assembly 12 from the left as noted in FIG. 1. Alternatively, wheel 100 could be placed into position by other devices, such as a crane and hook. As wheel 100 is rolled into position, sensors (not shown) in assembly 12 communicate a signal through ultrasonic test instrument 451 to CPU 450. Based upon the evaluation of the data, CPU 450 communicates a signal on one of lines 456 for actuation of cylinder 230 to move rod 270 for rotation of stopper 294 to contact wheel 100 and stop it in position over bridge support assembly 130, as well as first and second wheel runway assembly 140, 142 for subsequent transfer of wheel 100 to first and second rollers 150, 152 in tank 22. After retention in position on bridge assembly 130, CPU 450 communicates a signal to air cylinder 340, which is actuated to rotate bridge assembly 130, to lower wheel 100 onto first and second wheel runway assemblies 140, 142. Thereafter, air cylinders 300 of assemblies 140, 142 are actuated to extend rods 310 and lower wheel 100 into position on rollers 150, 152. Subsequently air cylinder 370 is actuated to extend rod 366 and sheave 360 to secure wheel flange 102 at an upper vertical position to maintain it in an upright posture during a test cycle.

Wheel 100 on sheaves 150, 152 is in position for test and evaluation of the subsurface of wheel tread 106. In this position, wheel 100 may be rotated as noted above by actuation of motor 204. However, it is to be noted that second transducer 416 is displaced from the horizontal by an acute angle 'a' in FIG. 4, which angle 'a' is the slope of the angular displacement of tread 106 from a horizontal plane. This slope or taper is thereby accommodated by the test apparatus to maintain transducer 416 at a normal or facing relationship to tread face 106. Initially the relative position of second transducer 416 is set by a signal sensed by first transducer 414 on rim face 108 in FIG. 4, which signal communicated to CPU 450 from ultrasonic test instrument 451 on line 452 is utilized to compare wheel face 106 to the standard wheel face to thus position second transducer 416 based upon the reference empirical data from the standardized or reference wheel data provided to CPU 450 at set up of the test apparatus for a particular wheel size. This evaluation then locates the center line of tread 106, which determines the travel distance of transducer 416 from rim face 108 toward flange 102 by CPU 450.

Second transducer 416 is thus about normal to the plane of tread 106. As first microstepper motor 406 moves arm 412 and transducer 416, an ultrasonic signal is imposed on wheel tread 106. The initial position of transducer 416 is a displacement from rim face 108 toward centerline 118, see FIG. 2, of wheel 100. Thereafter, wheel 100 is rotated in sheaves 150, 152 and 360 in its upright state and microstepper motor 406 incrementally indexes transducer 416 toward flange 102. In the preferred embodiment, wheel 100 is rotated through nine revolutions at a predetermined rate and simultaneously transducer 416 is indexed along tread 106 from rim face 108 to flange 102 at a rate of approximately 0.075 inch of lateral travel per wheel revolution, that will provide a travel range of about 0.675 inch along the surface of tread 106. The number of wheel revolutions may be varied by the operator to accommodate wheel size variations or other variables.

The ultrasonic signal is communicated through the transfer fluid in tank 22 to tread 106 to analyze the subsurface for various discontinuities or flaws such as changes in hot wheel cooling, which may induce parametric changes in the internal structure; inclusions from tramp casting sand (ceramic material); or, a void in the subsurface. Any of the above anomalies may result in a discontinuity exemplified by the presence of a reflected signal detected by transducer 416. The reflected signal, which may be compared to a reflected radar signal, provides a comparative signal to the empirical data provided to and stored in CPU 450 for internal analysis. Failure of the signal to provide indication of a sound wheel structure will result in exclusion or removal of test wheel 100 for further analysis.

The results of the test are monitored by CPU 450 and are reflected on an oscilloscope screen equipped with or connected to a printer for storage and retest alignment, an. In this test alignment, an example of a signal output is noted in FIG. 10 wherein the first column is the pulse number from transducer 416 onto tread 106. These output values are a percentage of the oscilloscope signal screen height. The wheel revolutions are noted along the top row of numbers, and there is a reflected output signal recorded on the hard copy output for each reflected signal above a pre-determined noise threshold greater than 5.

The signal has been clipped, that is, below a certain level of a reflected signal the sensed output is not recorded although there is a signal output from tread 106. At a signal output level greater than 5, which output is a percentage of the height of the signal shown on an oscilloscope screen, the digital equivalent of the signal is recorded on the hard copy. In the preferred embodiment, there are 9 revolutions of wheel 100 with an incremental travel distance of 0.075 inch of lateral travel per revolution of wheel 100 during a test cycle. The signals are not analyzed either near rim face 108 or flange 102 as the disparity in the mass of wheel 100 at these positions can affect signal output from transducer 416 and consequently blur the test results.

Figure 10A:
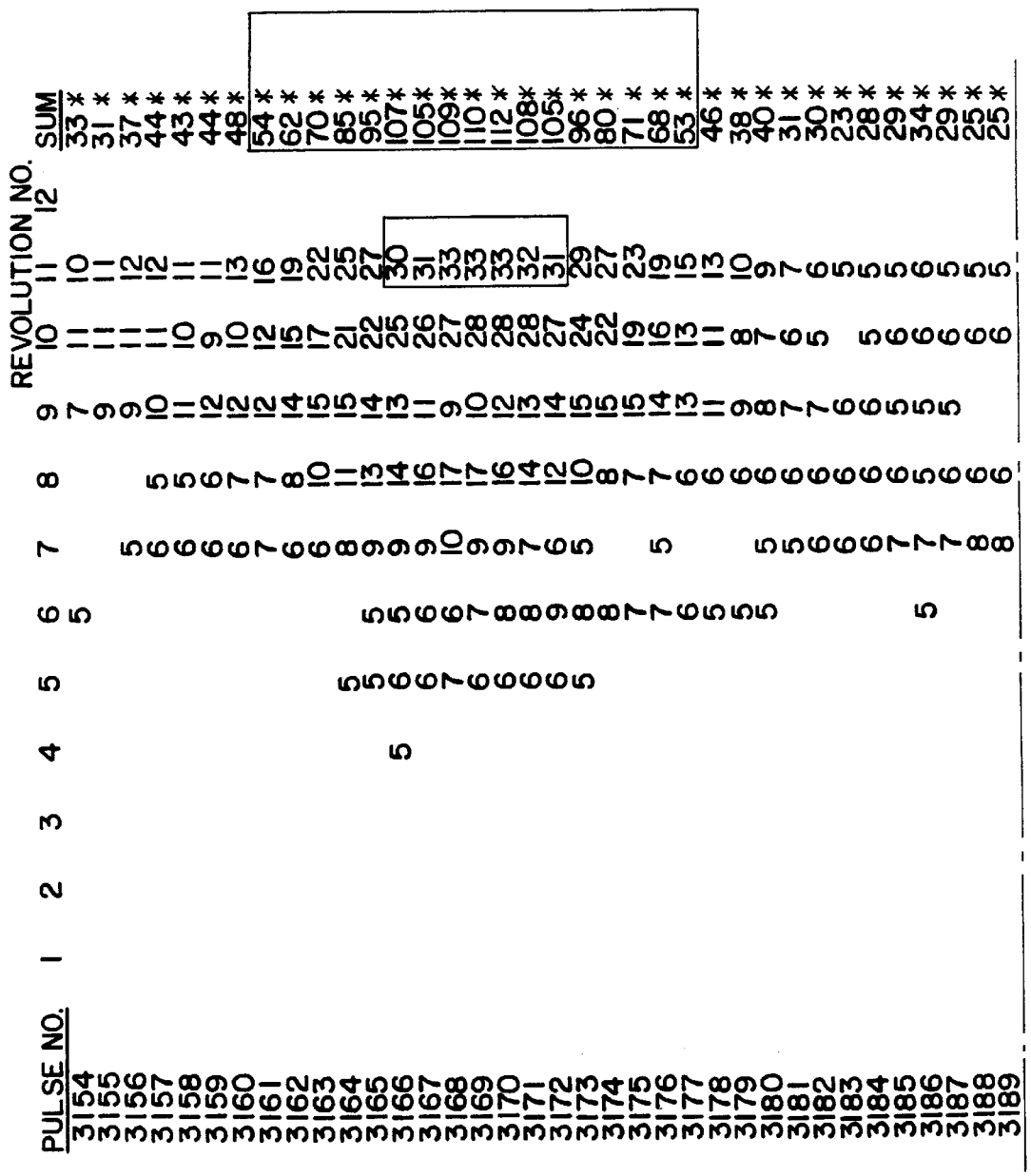
FIG. 10A is the upper half of an exemplary printout from an oscilloscopic output of a wheel test; and, FIG. 10B is the lower half of the exemplary oscilloscopic printout noted in FIG. 10A.

In the case of a signal height oscilloscope display in excess of a predetermined value, an alarm or other signal can imply an unacceptable product or indicate the requirement for rerunning the test. The final column in FIG. 10 illustrates a summation of the signal heights in any given column, that is a pulse number, and at a predetermined value or sum in this final column, wheel 100 can again be flagged for retest or reevaluation. The test provides a nondestructive evaluation of the internal soundness of a cast railway wheel 100, which evaluation is otherwise only detectable by discrete, single or multipoint evaluation. These earlier tests were not a continuous tread width evaluation of the wheel circumference, which also avoids the need for a destructive test. Further, the precise location of any discontinuities may be determined by physically noting a reference position on the wheel and thereafter repeating the evaluation. The test provides a practical means to provide a maximum test for added safety and consideration of the soundness of the wheel but also serves as an aid in evaluating the production process for quality analysis of earlier processes and tests.

While this invention has been described in connection with certain specific embodiments thereof, it is to be understood that this is by way of illustration and not by way of limitation; and the scope of the appended claims should be construed as broadly as the prior art will permit.

We claim:

1. A test apparatus for a railway wheel, which wheel has a subsurface structure, a front rim face, a flange with a flange face, and a tread face with a circumference and a tread-face width, said test apparatus comprising:

a housing having a frame assembly, a tank with a fixed volume mounted in said frame assembly, and an ultrasonic coupling fluid in said tank;

means for holding said wheel;

means for transferring said wheel to said holding means, said transferring means and said holding means operable to immerse at least a portion of said tread-face circumference in said tank;

means for rotating said holding means and said wheel to rotate said tread face through said coupling fluid in said tank;

means for transmitting an ultrasonic signal to said tread face;

means for sensing a responsive signal from said tread face through said coupling fluid;

means for positioning and moving said transmitting means and said sensing means;

means for controlling said rotating means, said transmitting means, said sensing means, said transferring means and said positioning means;

means for coupling said controlling means to said transmitting means, said sensing means, said transferring means, said positioning means and said rotating means, for communication of control signals to said transmitting means, sensing means, transferring means, positioning means and rotating means;

said transferring means operable to position said holding means with said wheel in said assembly and tank, and to remove said wheel from said holding means in response to said control signals from said controlling means;

said rotating means operable to rotate said wheel in said holding means in response to said control signals from said controlling means;

said positioning and moving means positioning said sensing means generally normal to said tread face and said positioning and moving means moving said transmitting means and sensing means generally across the tread-face width during rotation of said wheel; and said transmitting means and sensing means operable to transmit a signal to said tread face through said ultrasonic fluid and to sense a responsive signal from said tread face, said positioning and moving means moving said transmitting means and sensing means generally transverse to said tread face during a fixed number of revolutions of said wheel for communication of said sensed signal to said control means for the generation and storage of a mapped digest of ultrasonic subsurface structure of said wheel.

2. A test apparatus for a railway wheel as claimed in claim 1 wherein said tank has a bottom wall and a sidewall cooperating to define said tank and a fluid vat, said sidewall defining a first port and a second port;

said fluid in said vat having a fluid surface;

said means for holding said wheel having a first stub shaft and a second stub shaft, each said first and second stub shaft having a first end and a second end, one of said first and second stub shafts extending through one of said first and second ports in said tank sidewall, and the other of said first and second stub shafts extending through the other of said first and second ports in said tank sidewall, one of said first and second ends of each said first and second stub shafts positioned in said tank;

a first roller and a second roller, one of said first and second rollers mounted on one of said first and second shaft ends in said tank, and the other of said first and second rollers mounted on the other of said first and second shaft ends in said tank;

each of said first roller and second roller having a circumferential groove, which first roller groove and second roller groove are horizontally aligned and generally coplanar in said tank below said fluid surface;

a pneumatic operator with a reciprocating arm having a distal end, a third roller mounted on said distal end, which third roller has a circumferential groove horizontally aligned and generally coplanar with said first and second roller grooves at a reciprocating arm extended position;

said wheel flange nestable in said first and second roller grooves by said transferring means, said third roller positionable by said pneumatic operator above said wheel to engage said flange with said third roller groove, said first, second and third rollers operable to maintain said wheel in a plane;

said means for rotating coupled to at least one of said other of said first and second stub shaft ends to rotate said shaft and roller, and said wheel in said plane.

3. A test apparatus for a railway wheel as claimed in claim 1 wherein said transmitting means and said sensing means are transducers;

said positioning and moving means having an x-y table, a microstepper motor to move said table, and a mounting block;

said transmitting and sensing transducers mounted on said mounting block;

said x-y table positioning said transducers in proximity to said tread face and flange face, said stepper motor moving said transducers between said flange face and said wheel outer face in response to a signal from said controlling means.

4. A test apparatus for a railway wheel as claimed in claim 3 wherein said control means is a central processing unit.

5. A test apparatus for a railway wheel as claimed in claim 1 wherein said sensing means is generally normal to said tread face at a reference position and during said wheel rotation.

6. A test apparatus for a railway wheel as claimed in claim 5 wherein said holding means maintains said wheel in a plane, said positioning and moving means move said transmitting means and sensing means normal to said tread face during a fixed number of revolutions of said wheel in said holding means.

* * * * *